(12) United States Patent
Günther et al.

(10) Patent No.: US 8,348,846 B2
(45) Date of Patent: Jan. 8, 2013

(54) 3D MOTION DETECTION AND CORRECTION BY OBJECT TRACKING IN ULTRASOUND IMAGES

(75) Inventors: Jörg Matthias Günther, Bruchsal (DE); André Bongers, Hohenstein (DE)

(73) Assignee: Mediri GmbH, Heidelberg (DE)

( * ) Notice: Subject to any disclaimer, the term of this patent is extended or adjusted under 35 U.S.C. 154(b) by 90 days.

(21) Appl. No.: 13/121,419

(22) PCT Filed: Jun. 29, 2009

(86) PCT No.: PCT/EP2009/004678
§ 371 (c)(1), (2), (4) Date: Apr. 8, 2011

(87) PCT Pub. No.: WO2010/037436
PCT Pub. Date: Apr. 8, 2010

(65) Prior Publication Data
US 2011/0190629 A1 Aug. 4, 2011

(30) Foreign Application Priority Data

Sep. 30, 2008 (EP) .................. PCT/EP2008/008303

(51) Int. Cl.
*A61B 8/00* (2006.01)
(52) U.S. Cl. .......... 600/437; 600/443; 600/424
(58) Field of Classification Search ........ 600/424, 600/437–469; 382/128–132
See application file for complete search history.

(56) References Cited

U.S. PATENT DOCUMENTS

| | | | |
|---|---|---|---|
| 6,390,982 B1 | 5/2002 | Bova et al. | |
| 7,697,973 B2 * | 4/2010 | Strommer et al. | 600/424 |
| 7,742,802 B2 * | 6/2010 | Green et al. | 600/424 |
| 7,867,167 B2 * | 1/2011 | Boctor et al. | 600/437 |
| 7,912,258 B2 * | 3/2011 | Warmath et al. | 382/128 |
| 7,938,777 B2 * | 5/2011 | Amiot et al. | 600/437 |
| 8,135,198 B2 * | 3/2012 | Lachaine et al. | 382/131 |
| 8,152,726 B2 * | 4/2012 | Amiot et al. | 600/449 |
| 8,189,738 B2 * | 5/2012 | Dussault et al. | 378/65 |
| 8,235,909 B2 * | 8/2012 | Barthe et al. | 600/463 |
| 8,241,215 B2 * | 8/2012 | Takeuchi | 600/440 |
| 8,249,317 B2 * | 8/2012 | Falco et al. | 382/128 |
| 2005/0251029 A1 | 11/2005 | Khamene et al. | |
| 2006/0241443 A1 | 10/2006 | Whitmore, III et al. | |
| 2007/0015991 A1 | 1/2007 | Fu et al. | |

FOREIGN PATENT DOCUMENTS

| | | |
|---|---|---|
| DE | 19841859 A1 | 4/2000 |
| EP | 0647457 A1 | 4/1995 |
| GB | 2250164 A | 5/1992 |
| WO | 2006057911 A2 | 6/2006 |
| WO | 2006066792 A1 | 6/2006 |

OTHER PUBLICATIONS

English Abstract of DE 19841859 A1, Apr. 6, 2000.
English Abstract of EP 0647457 A1, Apr. 12, 1995.
English Abstract of WO 2006066792 A1, Jun. 29, 2006.
English Abstract of WO 2006057911 A1, Jun. 1, 2006.
Written Opinion of International Searching Authority, 2009.

* cited by examiner

*Primary Examiner* — Sanjay Cattungal
(74) *Attorney, Agent, or Firm* — Cahn & Samuels, LLP

(57) ABSTRACT

An arrangement to determine physiologic data, position, orientation and/or geometry of an object of interest includes an ultrasound unit with a multiplicity of ultrasound transducers to monitor physiologic parameters, especially motion and deformation, of an object of interest encapsulated by a body in real-time in three dimensions of space and to generate numerical control or trigger information for other medical devices.

28 Claims, 7 Drawing Sheets a)

b)

a)

b)

a)

b)

3D MOTION DETECTION AND CORRECTION BY OBJECT TRACKING IN ULTRASOUND IMAGES

This patent application is a U.S. national stage application of PCT international application PCT/EP2009/004678 filed on 29 Jun. 2009 and claims priority of PCT/EP2008/008303 filed on 30 Sep. 2008.

FIELD OF THE INVENTION

The present invention generally relates to the field of ultrasound imaging. In particular, it relates to an arrangement comprising an ultrasound system to determine physiologic data, position, orientation and/or geometry information of an object of interest in 3D using sparse 3D data acquired from a multiplicity of ultrasound transducers in real-time in order to control other medical devices.

BACKGROUND OF THE INVENTION

In many medical applications such as medical imaging and radiation therapy the quality of the outcomes is significantly impaired by patient and organ motion. Especially in abdominal radiation therapy patient and organ movement is a crucial factor.

The accuracy of current radiation methods lies well within the millimeter range. However, in clinical practice the achievable precision of radiation therapy when irradiating a tumor within the abdomen is largely reduced due to motion induced by breathing, heart beat and intestine peristalsis. Due to the mentioned motion the irradiated volume has to be increased by an additional margin to ensure sufficient (i.e. the prescribed) radiation dose within the diagnosed tumor volume. This margin usually has to be chosen in the range of several centimeters so that organs at risk suffer from a significantly elevated exposure to radiation. To minimize the required radiation dosage the motion of the irradiated object has to be controlled and/or corrected for.

DESCRIPTION OF RELATED ART

In standard therapy setups there are different breath holding techniques in operation that limit a single radiation exposure to 20 s or less which are administered during breath hold. Repeated breath holding phases are then used to reach higher dose levels.

Current clinical state of the art radiation sites also use more sophisticated techniques applying breathing belts or sensors to control current breath status and then trigger the accelerator. However, all of theses methods suffer from the disadvantage that they do not observe the motion itself but use a very indirect correlate. Hence, they crucially have to rely on a reproducible positioning of structures during several breathing phases and are not able to control the actual position of the object of interest. Since they only trigger the radiation beam the accelerator is idle most of the therapy session waiting for the correct breath hold state of the patient. This significantly prolongs the therapy and very much reduces its time efficiency.

Some recent methods aim to measure tissue motion in real time or near-real time and correct for it. One approach currently in use is to follow motion of the chest walls by optical methods and to infer from these data the motion of internal structures. This can be done by optical methods using laser scanning or stereoscopic tracking of external markers. However, the conclusion from such external motion information to displacements of internal organs is not easily possible since these are often—if at all—not very well correlated.

Currently there are also attempts to observe and measure motion with more direct approaches. The commercially available state-of-the-art techniques mainly use stereoscopic x-ray imaging to image internal structures and match images to determine displacements during the therapy session. However, since these methods rely on ionizing radiation they add dose to the patients treatment plan and cannot be performed in real-time without seriously harming the patient. This is why they are primarily used only for repositioning and intermittent position verification (e.g. every minute) but not for real motion tracking. The inherently low soft-tissue contrast of x-rays also limits the usability of these methods to dense structure matching, so that often the implantation of internal markers in an invasive procedure is necessary. These limitations largely restrict the application of x-ray methods to the research environment or special patient groups.

A promising modality to enable motion detection and correction for internal structures is ultrasound imaging. Ultrasound has the advantage that it is non invasive, non-harming for the patient and capable for true real-time motion detection and tracking.

An embodiment to improve radiation dosimetry is disclosed by the patent WO 2006/066792 A1, Putaala, Elekta: "Radiotherapeutic Apparatus". The suggested setup uses ultrasound imaging in the stereotactic frame of the linear accelerator to generate volumetric tissue data. This approach aims at classifying tissue types in terms of radiotherapeutic density values. These values are used as a substitute or complement of CT planning data in order to determine a dispersion of the radiation doses prior to the radiation dosimetry procedure. The disclosed embodiment cannot determine values in real-time. In particular, it cannot be applied to detect and compensate organ motion.

US 2002/6390982 B1 Bova, Friedman, Meeks, Buatti: "Ultrasonic guidance of target structures for medical procedures" discloses the use of ultrasound between subsequent radiotherapeutic fractions of a radiation plan to verify the localization of soft tissue structures as a complement to the standard inter-fractional cone-beam CT at the therapeutic site. The CT determines the position of rigid bone structures prior to the application of a single dose fraction. Ultrasound additionally locates organs moving relative to the bone. The ultrasound data is registered from a single 3D transducer to a fixed frame of reference defined by the iso-center system of a radiation therapy site. The ultrasound volume is combined with data from another imaging modality (e.g. the planning CT) registered to the same fixed frame of reference. The overlay of both data-sets can be used by the medical staff to correct initial positioning errors before each therapy fraction. The aim of the invention is to reduce repositioning errors between radiation therapy fractions to complement CT repositioning Systems. Accordingly, motion correction during radiation therapy, particularly real-time motion correction, is not disclosed.

US 2007/0015991 A1 Fu, Kuduvalli, Accuray: "Dynamic Tracking of soft tissue targets with ultrasound images without using fiducial markers" suggests to register an ultrasound image with a CT image to determine initial replacements and also to register two subsequent ultrasound images to facilitate motion detection. This patent describes ultrasound motion registration in non-real time complemented by real-time tracking of external optical markers. A correlation model is applied to deduce organ motion. Since this method determines the organ motion in an indirect way the results are not sufficiently precise.

US 2006/0241443 A1 Whitmore, Schenk, Onik: "Real time ultrasound monitoring of the motion of internal structures during respiration for control of therapy delivery" e.g. claims a device to do real-time tracking in 2D. However, besides the fact that it does not give a feasible solution for structure tracking on ultrasound images (Only a very basic correlation method is suggested which appears be slow and not robust enough for ultrasound tracking.) it only uses a single 2D ultrasound transducer on a fixed bracket. In such a single-view approach moving structures of interest tend to leave the viewing window of the ultrasound transducer and cannot be continuously examined. Also the sound window can easily be obscured by hyper- or hypo-dense structures (e.g. bones or air). Due to the fixed clamp the transducer can easily loose contact with the patient. The 2D technique can only measure object displacements within the ultrasound plane and hence is not suited for online-monitoring of organ motion in 3D.

Devices with a single 3D ultrasound transducer cannot be used to realize object tracking feasible for clinical application. Similar to arrangements with two-dimensional transducers described above, for single view 3D methods the risk of loosing or masking structures remains. 3D datasets are very large in size. The huge amount of data impedes the application of effective tracking methods, Electronically swept 3D transducers are very expensive and quite massive. 3D transducers which are affordable for practical use comprise a mechanism to mechanically sweep through the 2D image planes. Hence, those transducers are not real-time capable. Like electronically swept transducers, mechanical transducers are furthermore quite massive, so they have to be mounted on a fixed clamp with the risk of loosing contact to the patient.

Problem

The preferable properties of ultrasound recommend the use of an ultrasound device to monitor physiologic data, position, orientation and/or geometry of an organ in order to control medical devices, such as accelerators for radiation therapy. Embodiments according to the current art
- limit the duration of a radiation exposure,
- cause idle time of the accelerator,
- lack of precision,
- harm the patient due to additionally required doses of radiation,
- are not able to observe motion directly but have to use indirect correlates
- cannot detect soft-tissue with a sufficiently high contrast
- tend to loose contact to the patient's body,
- are too expensive for clinical use,
- cannot retrieve tree-dimensional data,
- are deranged by hyper- or hypo-dense structures
- loose sight of objects, if they move, and/or
- cannot provide data in real-time.

Currently, no system exists which is able to directly monitor vital parameters and/or tissue motion inside a patient during radiation therapy to control motion in real-time.

SUMMARY OF INVENTION

In order to overcome the deficiencies and inconveniencies of the prior art the present invention provides an arrangement to determine physiologic data, position, orientation and/or geometry of an object of interest. The arrangement comprises an ultrasound unit with one or more ultrasound transducers (an ultrasound system), also referred as ultrasound probes or sonographic transducers, a position detection system and a processing unit. The position detection system detects the position and/or orientation of each of the one or more ultrasound transducers. From ultrasound data provided by the ultrasound unit and from position and/or orientation information provided by the position detection system the processing unit calculates physiologic data, position, orientation and/or geometry of the object of interest compensating for induced movements, such movements induced by breathing or by heart beat.

Initially, the data acquired by the one or more ultrasound transducers refer to a frame of reference defined by the spatial position of the one or more ultrasound transducers. This data can be transferred to a common frame of reference by charging the ultrasound data against information about the position and/or orientation of each of the one or more ultrasound transducers detected by the position detection system. As a result, the physiologic data, position, orientation and/or geometry of the object of interest calculated by the processing unit refer to that common frame of reference.

The physiologic data, position, orientation and/or geometry of the object of interest can be any information derivable from ultrasound data, especially motion information in terms of velocity (temporal derivation of a spatial position) or in terms of a sequence of position information. Motion information concerning breathing, heartbeat or peristalsis is of special interest. Preferably, the motion information is gained from the measurement of structure displacements in ultrasound image series. Doppler signals can be used to complement this information with velocity information. From these measurements also additional information about the orientation of objects, information about deformation of objects and/or information about flow, particularly blood flow, can be determined. Preferably, the information derived from the ultrasound data spans a three-dimensional space.

A preferred arrangement comprises more than one ultrasound transducer to simultaneously or nearly simultaneously view a structure of interest from different perspectives and positions. Due to the "multi-view" dataset provided by more than one ultrasound transducer objects which are in motion can be continuously examined without leaving the viewing window of the ultrasound transducers. By arranging the more than one ultrasound transducers in such a way that they provide redundant sound windows, hyper- or hypo-dense structures (e.g. bones or air) can be obviated from obscuring the sound window. The "multi-view" dataset also enables the acquisition of vital parameters (e.g. motion) that span a three-dimensional space even with ultrasound transducers of lower data-dimensionality (i.e. ultrasound transducers with one-dimensional or two-dimensional data acquisition capabilities) In this way it is possible to retrieve three-dimensional information of the time evolution of the object using multiple transducers with two-dimensional or one-dimensional data acquisition capabilities.

Preferably, the calculation of the physiologic data, position, orientation and/or geometry of the object of interest is performed by the arrangement in real-time. Real-time denotes a certain characteristic of an information processing system, wherein the system is continuously ready for processing an input signal and calculating an output signal. The time required for calculating the output signal (delay) must not exceed a certain predefined period of time (upper bound delay). For Hard real-time systems, a delay exceeding the upper pound delay is assessed as a critical failure. Soft real-time systems tolerate such lateness, and may usually respond with decreased service quality. The arrangement can be a hard-real time system or a soft real-time System. In order to control medical devices, a short delay is of particular importance. To compensate for slow movements, such as movements induced by breathing, the arrangement realizes an average delay and/or an upper bound delay of less than 100 ms. An average delay and/or an upper bound delay of less than 25 ms is realized to compensate for quick movements, such as movements induced by heart beat The one or more ultrasound transducers can be sonographically coupled to the body encapsulating the object of interest. Especially, this body can be the body of a patient. The object of interest can be an organ or any object which is of interest in industrial applications (e.g. machine part, etc.).

In a preferred embodiment, the one or more ultrasound transducers are attached to the object of interest or to the body encapsulating the object of interest. If the object of interest is not encapsulated by a body, the one or more ultrasound transducers can be directly attached to the object of interest. Otherwise, if the object of interest is encapsulated by a body, the one or more ultrasound transducers can be attached to the body. This ensures that the one or more ultrasound transducers directly follow the movements of the object of interest or the body encapsulating the object of interest and hence prevents the one or more transducers from loosing contact to the object of interest or body. Loosing contact to the object of interest or body would derogate the transmission of ultrasound signals generated by the transducers.

When attached to the object of interest or to the body encapsulating the object of interest one or more of the ultrasound transducers may move independently from each other.

The freedom of movement of one or more of the ultrasound transducers can be restricted with respect to each other. Restricting the movement between two of the one or more ultrasound transducers means restricting one or more of the six possible degrees of movement between the two ultrasound transducers. Restricting the movement of one or more of the ultrasound transducers with respect to each other results in one or more groups of ultrasound transducers, wherein each group consists of one or more ultrasound transducers whose freedom of movement is restricted with respect to each other. In particular, the freedom of movement of each of the groups of transducers as a hole is not restricted. In a preferred embodiment, the freedom of movement of all of the one or more ultrasound transducers is restricted with respect to each other.

In another preferred embodiment, one or more of the ultrasound transducers are connected to a frame of reference in such a way that the freedom of movement of those ultrasound transducers is restricted with respect to the frame of reference. In particular, not each ultrasound transducer has to be connected to the frame of reference. Those ultrasound transducers which are not connected to the frame of reference can be connected to other ultrasound transducers, i.e. the freedom of movement of each of the ultrasound transducers which are not connected to the frame of reference is restricted with respect to one or more other ultrasound transducers. The frame of reference can be provided by any equipment aside from the object of interest or the body encapsulating the object of interest.

Preferably, the processing unit matches a set of one or more reference models representing certain structures of the object of interest to each frame of ultrasound data provided by the ultrasound unit. A frame of ultrasound data denotes a set of ultrasound data with temporal coherency, i.e. a set of ultrasound data representing the state of the object of interest at a certain point in time. The one or more ultrasound transducers sequentially acquire different frames of ultrasound data and transfer them to the ultrasound unit. The ultrasound unit provides the processing unit with these frames of ultrasound data.

Any information about the object of interest which is a-priori known may be encoded by the one or more reference models and gained from the one or more reference models by the processing unit. The one or more reference models can be parametrizable: Certain parameters of the models are variable. Several of the variable parameters (specifiable parameters) can be defined by the processing unit, whilst the values of the remainder of the variable parameters are calculated depending on the actual value of the specifiable parameters. To match the set of one or more reference models to a frame of ultrasound data provided by the ultrasound unit the processing unit defines the specifiable parameters in such a manner that their values resemble corresponding data from the frame of ultrasound data. By using the one or more reference models, information can be provided by the processing unit which is not enclosed by the ultrasound data. E.g. ultrasound data coming from multiple transducers of lower data-dimensionality can be used to fit the model—which then provides full three-dimensional information. This means that the acquisition of sparse ultrasound data is sufficient to gain three-dimensional information about vital parameters. This significantly accelerates the data acquisition process and reduces the time for parameter calculation so that the retrieval of three-dimensional information is possible in real-time.

Preferably, the one or more reference models are three-dimensional, i.e. represents three-dimensional structures of the object of interest.

The information gained from the set of one or more reference models is preferably used by the processing unit to calculate the physiologic data, position, orientation and/or geometry of the object of interest.

In a preferred embodiment, the set of one or more reference models comprises more than one reference model. The information to calculate the physiologic data, position, orientation and/or geometry of the object of interest can be gained by the processing unit from a weighted average of the more than one reference model. The weighted average can, for example, be calculated from probability values assigned to each of the more than one reference model.

Preferably, the processing unit gains information from a sequence of several sets of one or more reference models. Each of the sets of one or more reference models is matched by the processing unit to a different frame of ultrasound data, wherein the different frames of ultrasound data are sequentially acquired by the one or more ultrasound transducers. Based on differentials between subsequent sets of one or more reference models temporal variations of the physiologic data, position, orientation and/or geometry, such as movements or deformation, of the object of interest can be determined. The processing unit can particularly gain information from a sequence of several sets of more than one reference model, wherein the processing unit calculates the weighted average of the more than one reference model.

In a preferred embodiment, each set of one or more reference models is estimated based on the previous set of one or more reference models: A second set from the sequence of several sets of one or more reference models is built by the processing unit based on a first set from the sequence of several sets of one or more reference models. The first set is matched to a first frame of ultrasound data and the second set is matched to a second frame of ultrasound data, wherein the second frame of ultrasound data is acquired by the one or more ultrasound transducers subsequently to the first frame of ultrasound data. The initial set within the sequence of several sets of one or more reference models can be built by random transformations of an initial reference model. Each set within the sequence of reference models following the initial set can be estimated based on the previous set by a stochastic procedure.

In a further preferred embodiment, the weights for calculating the weighted average for each set within the sequence of several sets of one or more reference models is propagated by a autoregressive model: The weights for calculating the weighted average of the one or more reference models of a first set from the sequence of several sets of one or more reference models are propagated by the processing unit to calculate the weighted average of the one or more reference models of a second set from the sequence of several sets of one or more reference models. The first set is matched to a first frame of ultrasound data and the second set is matched to a second frame of ultrasound data, wherein the second frame of ultrasound data is acquired by the one or more ultrasound transducers subsequently to the first frame of ultrasound data. Building sets of one or more reference models based on preceding sets of one or more reference models and propagating the weights for calculating the weighted averages increases the robustness against clutter and noise within the ultrasound data.

In order to configure the one or more reference models and set up the parameters which are not specifiable by the processing unit appropriate for use with the actual kind of object of interest, the one or more reference models can be derived from image data acquired by a second imaging modality (an imaging modality apart from the ultrasound unit; e.g. CT, MR or PET), from ultrasound speckle patterns, from a radiation plan, from user input and/or from an abstract model of structures. The calculation of physiologic data, position, orientation and/or geometry of the object of interest performed by the processing unit does not require the ultrasound data acquired by the one or more ultrasound transducers to be complete. Instead, the ultrasound data can be sparse. The term "sparse" is well known to a person skilled in the art. A sparse matrix is generally defined as a matrix with a multiplicity of zero entries. Accordingly, the sparse ultrasound data acquired by the one or more ultrasound transducers is constituted by a set of data entities, each entity assigned to a spatial position, where a multiplicity of spatial positions within the space captured by the object of interest is not assigned a data entity. Information related to that multiplicity of spatial positions, which may be required to calculate the physiologic data, position, orientation and/or geometry of the object of interest, can be extrapolated from the one or more reference models. Even if less than one half of the space captured by the object of interest is assigned an entity of ultrasound data, the calculation of physiologic data, position, orientation and/or geometry of the object of interest can be performed.

In a preferred embodiment, the claimed arrangement comprises one or more ultrasound transducers with three-dimensional data acquisition capabilities. These ultrasound transducers acquire the ultrasound data from one or more tree-dimensional volumes. The ultrasound data can be sparse or complete.

In an alternative preferred embodiment, the claimed arrangement comprises two or more non-coplanar ultrasound transducers with two-dimensional data acquisition capabilities. These two or more ultrasound transducers acquire sparse ultrasound data from two-dimensional slices.

In a further alternative preferred embodiment, the claimed arrangement comprises three or more non-collinear ultrasound transducers with one-dimensional data acquisition capabilities. These three or more ultrasound transducers acquire sparse ultrasound data from one-dimensional rays.

To determine the position and/or orientation of each of the one or more ultrasound transducers a preferred embodiment of the position detection system comprises one or more position sensors, wherein each of the on or more position sensors is attached to one of the one or more ultrasound transducers.

Several embodiments of the one or more position sensors attached to the one or more ultrasound transducers can be realized. In a first preferred embodiment, at least one of the position sensors is electromagnetically non-transparent. This enables the position and/or orientation of the one or more ultrasound transducers which are attached with one of the electromagnetically non-transparent position sensors to be detected when arranged in an electromagnetic field, for example when arranged in a MRT-Device or to be detected using an electromagnetic tracking system (such as the Aurora system provided by NDI, for example).

In a second preferred embodiment, at least one of the position sensors is a motion, acceleration and/or ankle sensor to determine motion, acceleration and/or ankle information of the one or more ultrasound transducers which are attached with one of the at least one motion, acceleration and/or ankle sensors. Electromagnetically non-transparent sensors and motion, acceleration and/or ankle sensor can be applied simultaneously, meaning that at least one of the position sensors is electromagnetically non-transparent and at least one of the position sensors is a motion, acceleration and/or ankle sensor. This increases the precision of the determined motion, acceleration and/or ankle information of the one or more ultrasound transducers.

In another preferred embodiment, the position detection system comprises one or more optical cameras to determine the position and/or orientation of each of the one or more ultrasound transducers. These optical cameras record the one or more ultrasound transducers. The position and/or orientation of each of the one or more ultrasound transducers can be determined by means of object recognition methods or by means of markers attached to the one or more ultrasound transducers. Preferably, the optical cameras and the position sensors can be applied simultaneously, meaning that the position detection system comprises one or more optical cameras and one or more position sensors, such as electromagnetically non-transparent sensors, motion, acceleration and/or ankle sensors, wherein each of the on or more position sensors is attached to one of the one or more ultrasound transducers. This increases the precision of the determined motion, acceleration and/or ankle information of the one or more ultrasound transducers.

Furthermore, a method to determine physiologic data, position, orientation and/or geometry of the object of interest is claimed. This method calculates physiologic data, position, orientation and/or geometry of the object of interest from ultrasound data and from position and/or orientation information referring to the position and/or orientation of the ultrasound transducers comprised by the arrangement delineated above. In particular, the arrangement delineated above can be applied to perform the claimed method.

Preferably, the claimed method calculates the physiologic data, position, orientation and/or geometry of the object of interest in real-time.

Preferably, the claimed method matches a set of one or more reference models representing certain structures of the object of interest to each frame of ultrasound data.

Preferably, the claimed method gains information from the one or more reference models and calculates the physiologic data, position, orientation and/or geometry of the object of interest based on the information gained from the one or more reference models.

Preferably, the set of one or more reference models comprises more than one reference model, wherein the claimed method gains the information to calculate the physiologic data, position, orientation and/or geometry of the object of interest from a weighted average of the more than one reference model.

Preferably, the claimed method gains information from a sequence of several sets of one or more reference models, each set matched to a different frame of ultrasound data, wherein the different frames of ultrasound data are acquired sequentially. The information gained from the sequence of several sets of one or more reference models is preferably used by the claimed method to determine temporal variations of the physiologic data, position, orientation and/or geometry of the object of interest.

Preferably, a second set from the sequence of several sets of one or more reference models is built by the claimed method based on a first set from the sequence of several sets of one or more reference models, wherein the first set is matched to a first frame of ultrasound data and the second set is matched to a second frame of ultrasound data, wherein the second frame of ultrasound data is acquired subsequently to the first frame of ultrasound data.

Preferably, weights for calculating the weighted average of the one or more reference models of a first set from the sequence of several sets of one or more reference models are propagated by the claimed method to calculate the weighted average of the one or more reference models of a second set from the sequence of several sets of one or more reference models, wherein the first set is matched to a first frame of ultrasound data and the second set is matched to a second frame of ultrasound data, wherein the second frame of ultrasound data is acquired subsequently to the first frame of ultrasound data.

Preferably, the claimed method derives the one or more reference models from image data acquired by a second imaging modality (an imaging modality apart from the ultrasound unit comprised by the arrangement to determine physiologic data, position, orientation and/or geometry of the object of interest delineated above; e.g. CT, MR or PET), from ultrasound speckle patterns, from a radiation plan, from user input and/or from an abstract model of structures.

The claimed method is capable of calculating the physiologic data, the position and/or the geometry of the object of interest from sparse three-dimensional ultrasound data.

Preferably, the claimed method gains the position and/or orientation information referring to the position and/or orientation of the ultrasound transducers comprised by the arrangement delineated above from electromagnetic signals generated by electromagnetically non-transparent position sensors, from motion, acceleration and/or ankle signals generated by motion, acceleration and/or ankle sensors and/or from optical signals generated by optical cameras.

Furthermore, a computer program product is claimed. This computer program product has program code means, which can be stored or are stored on a storage medium, for performing the claimed method delineated above, if the program code means are executed on a computer or on a computer network.

The claimed arrangement delineated above, the claimed method delineated above and/or the claimed computer program product delineated above can be used to control a medical device, such as a radiation therapy device, an imaging device or surgical or biopsy instruments. In particular, the claimed arrangement, the claimed method and/or the claimed computer program product can be used to generate trigger signals, exclusion and inclusion signals or continuous control signals for the medical device.

Even if no multiple back-referenced claims are drawn, all reasonable combinations of the features in the claims shall be disclosed.

BRIEF DESCRIPTION OF THE SEVERAL VIEWS OF THE DRAWINGS

Other objects and advantages of the present invention may be ascertained from a reading of the specification and appended claims in conjunction with the drawings therein. The drawings are to be regarded in an illustrative rather than in any restrictive sense.

For a more complete understanding of the present invention, reference is established to the following description made in connection with accompanying drawings in which.

DETAILED DESCRIPTION OF THE INVENTION

Figure 1:
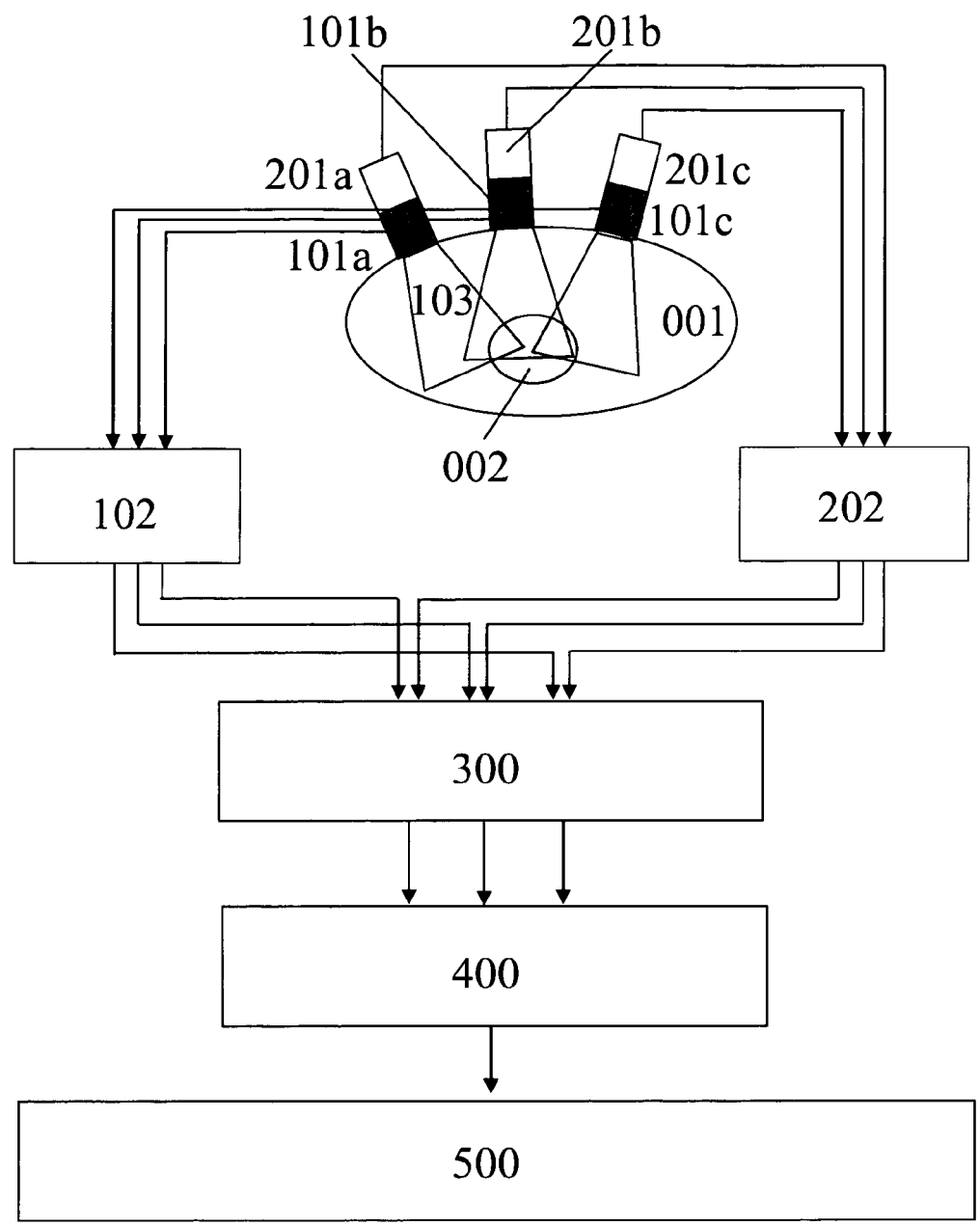
FIG. 1 shows an embodiment of the invention with three ultrasound transducers.

As delineated in FIG. 1, a preferred embodiment of the claimed invention comprises the following components:

a) an ultrasound unit 102 (including a transmit and receive unit) providing structural and/or physiologic data in real-time;

b) one or more one 1D (one-dimensional), 2D (two-dimensional) or 3D (three-dimensional) ultrasound transducers 101*a*, 101*b*, 101*c* coupled to the ultrasound unit 102 to provide linearly independent (i.e. acquired from different directions, in multiple non-coplanar planes or non-collinear lines) sparse or complete 3D ultrasound data. The ultrasound transducers 101*a*, 101*b*, 101*c* can be pasted directly to the body 001 or be mounted to the body 001 in a different way. Furthermore, they can be either fixed with respect to the reference frame or float freely;

c) a system 201*a*, 201*b*, 201*c*, 202 to continuously determine the localization and viewing direction of each ultrasound transducer 101*a*, 101*b*, 101*c* relative to a fixed frame of reference;

d) a system 300 to transform ultrasound data from the individual coordinate systems defined by the ultrasound transducers 101*a*, 101*b*, 101*c* into a common fixed frame of reference.

e) a system 400 to extract three dimensional physiologic (e.g. motion) information from the data acquired by the ultrasound transducers 101*a*, 101*b*, 101*c* in real-time.

Ultrasound Unit 102 and Ultrasound Transducers 101*a*, 101*b*, 101*c*

The transducers 101*a*, 101*b*, 101*c* are coupled to an ultrasound transmit/receive unit 102 which is able to control and to acquire data from multiple transducers 101*a*, 101*b*, 101*c* simultaneously or nearly simultaneously. The data optionally can (but not necessarily has to) be reconstructed to form image lines, 2D images or 3D image volumes depending of the transducer geometry.

The ultrasound unit 102 collects data from an observed object of interest 002. The ultrasound unit 102 is connected to one or more ultrasound transducers 101a, 101b, 101c with 1D, 2D or 3D data acquisition capabilities. (i.e. transducer arrays of dimensionality 0D, 1D, 2D, respectively) The ultrasound transducers 101a, 101b, 101c collect data indicative for the location, deformation or physiologic status of a region of interest. These data are subsequently transferred to the ultrasound unit 102 for further processing. In certain embodiments the data can be reconstructed to form image lines (1D), images (2D) or image volumes (3D). In other embodiments the RF data may be used directly without prior reconstruction.

The transducers 101a, 101b, 101c may have several geometries but are generally arranged so that their data collection directions span a 3 dimensional space. I.e. when 1D ultrasound transducers 101a, 101b, 101c are used, there are at least 3 or more non-collinear transducers 101a, 101b, 101c necessary. In the case of 2D transducers 101a, 101b, 101c at least 2 or more non-coplanar transducers 101a, 101b, 101c are required. In the case of 3D transducers 101a, 101b, 101c at least one transducer 101a, 101b, 101c is required.

The transducers 101a, 101b, 101c can either be fixed relative to the common frame of reference on an arm or they can be free floating e.g. on the surface of the patient's body 001.

Figure 2:
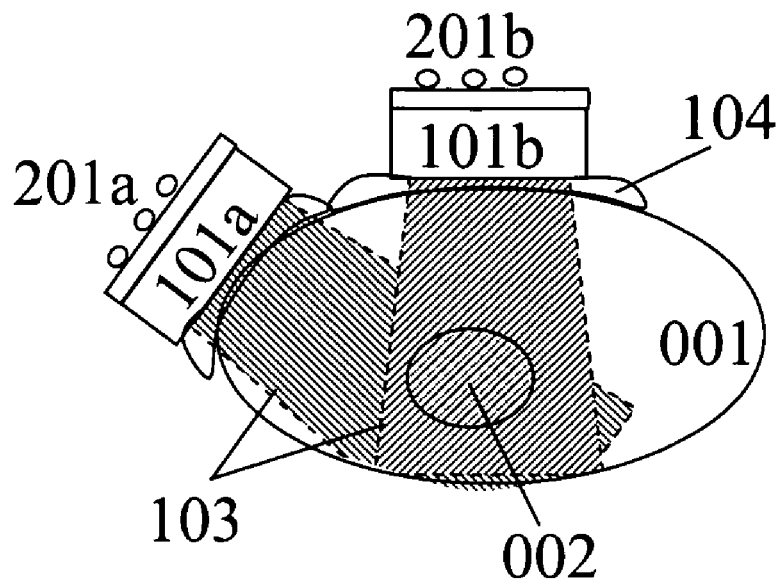
FIG. 2 shows an embodiment of the invention with independent ultrasound transducers with different view angles and positions.
Figure 2:
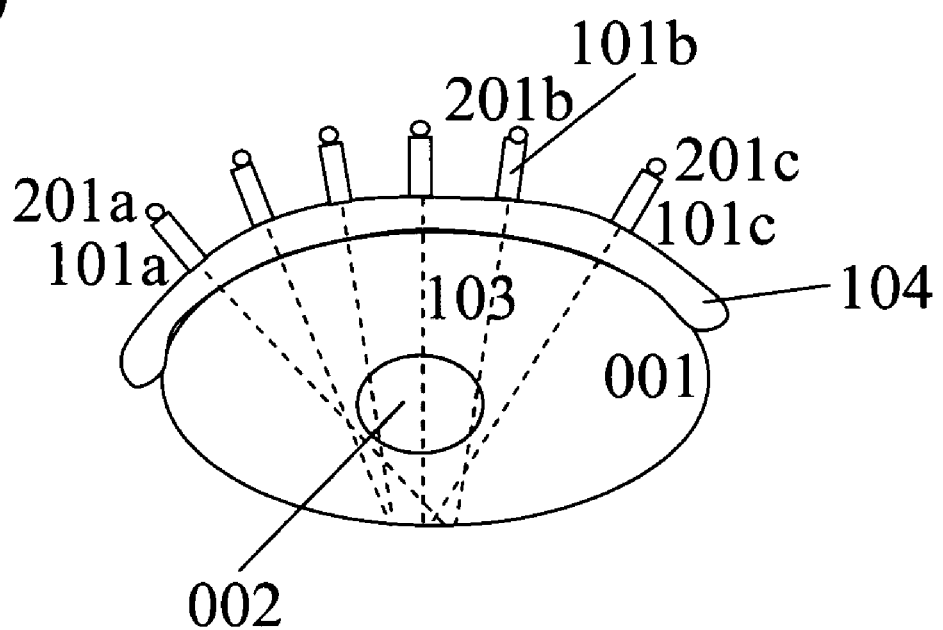

In a preferred embodiment the ultrasound transducers 101a, 101b, 101c have more than one independent positions and/or directions so that the general problem of loosing the structure of interest in the viewing window is solved. According embodiments are depicted in FIG. 2.

FIG. 2a) shows an example with two 2D or 3D transducers 101a, 101b with attached position sensors 201a, 201b. The transducers 101a, 101b are acoustically coupled to the body surface of a patient 001. The coupling to the body surface can e.g. be done by gel pads or other coupling devices 104. In some embodiments the gel pads 104 or the transducer surface may be self-adhesive so that the transducers 101a, 101b, 101c can be pasted directly to the body 001. In such an embodiment, the transducers 101a, 101b can move freely when the patient body's surface is moving. Each of the transducers 101a, 101b produces either 2D image planes or 3D data volumes 103 so that sparse or redundant 3D information about the physiologic state of the organ 002 can be collected.

FIG. 2b) shows a similar embodiment with multiple independent 1D transducers (i.e. transducers producing 1D ultrasound rays) 101a, 101b, 101c mounted on an acoustic coupling device 104. The position of each transducer 101a, 101b, 101c is determined individually by an individual position sensor 201a, 201b, 201c. Each individual transducer 101a, 101b, 101c produces a 1D ultrasound ray 103 so that with at least 3 sensors of this kind a sparse 3D dataset with 3D information of the structures' physiologic status can be obtained.

Figure 3:
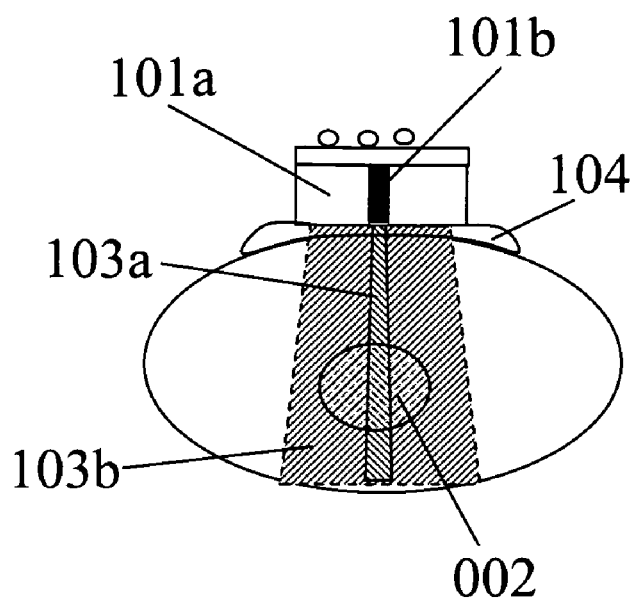
FIG. 3 shows rigidly coupled non-collinear ultrasound transducers.
Figure 3:
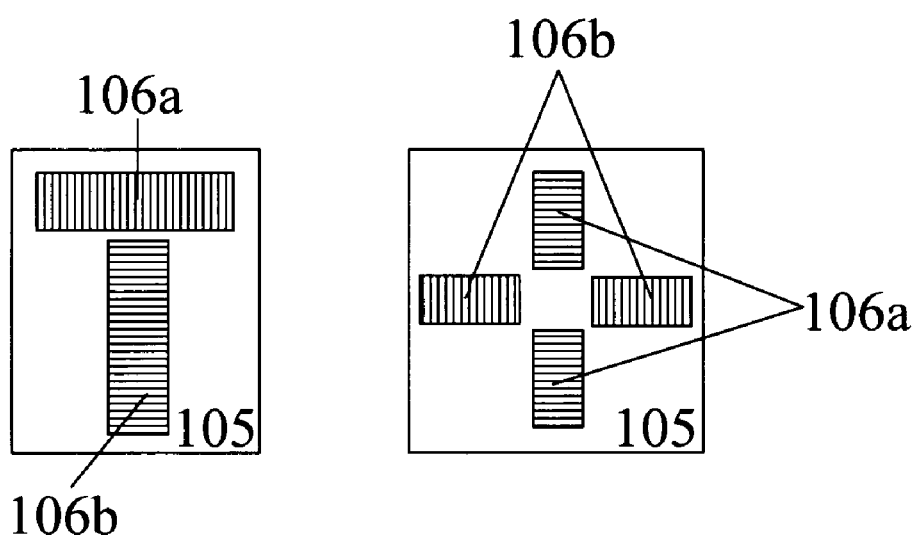

FIG. 3 shows an embodiment of transducers 101a, 101b which are installed in a fixed spatial relationship to each other. E.g. 2D transducer arrays can be fixed in a common case 105 with a certain angle to each other in order to effectuate a fixed relationship of the resulting ultrasound data. A feasible transducer geometry is e.g. a T- or cross shaped mounting of linear or phased array transducers 106a, 106b in a common transducer case 105 as depicted in FIG. 3b).

Figure 4:
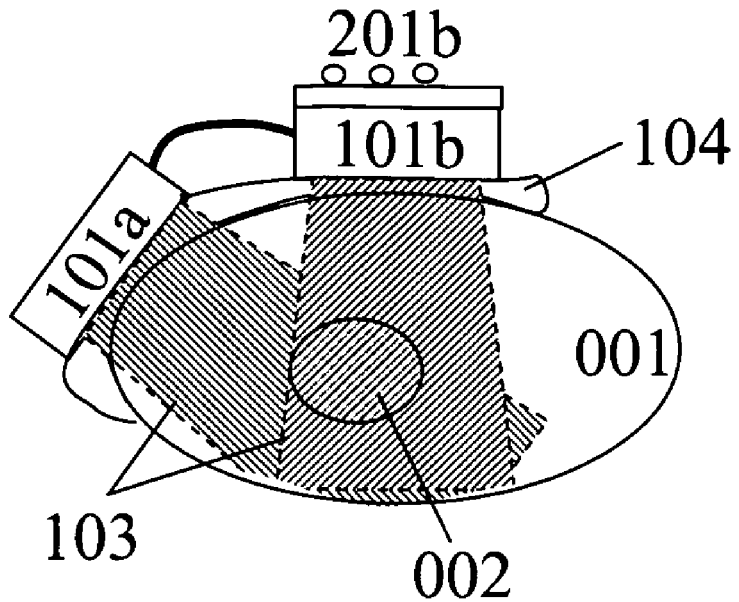
FIG. 4 shows an embodiment of the invention with independently moving, coupled ultrasound transducers.
Figure 4:
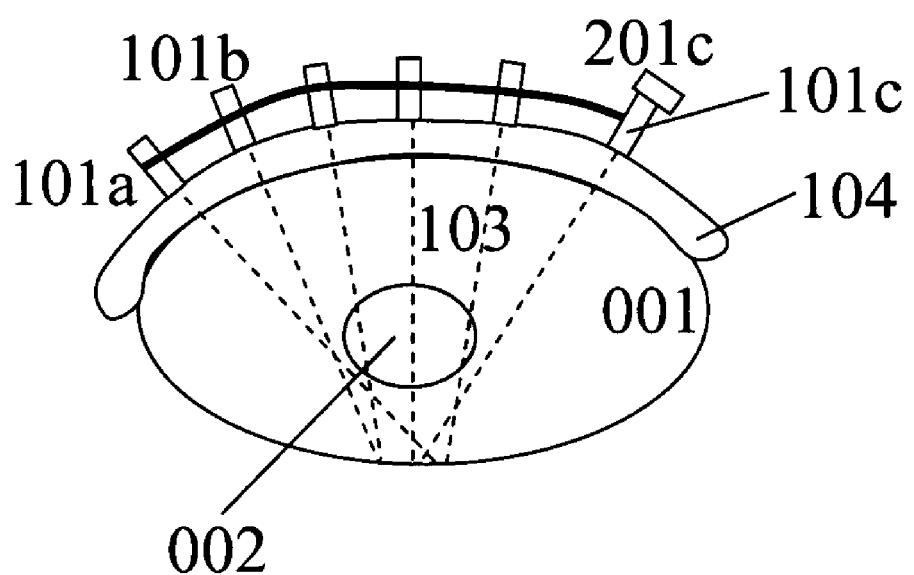

FIG. 4a) shows an example with two 2D or 3D transducers 101a, 101b acoustically coupled to the body surface of a patient 001 via an acoustic coupling device 104. In this example only the position and orientation of a reference transducer 101b is monitored in absolute world (room) coordinates by the position sensor 201b attached to the reference transducer 101b. The position and orientation of a second transducer 101a is determined relative to the reference transducer 101b. This relative measurement can be done by a strain gauge, electromagnetic or other means. From the absolute position and orientation of the reference transducer 101b and the relative position and relative orientation of the second transducer 101a the position and orientation of the second transducer 101a in absolute world coordinates can be calculated.

FIG. 4b) shows a similar embodiment with multiple independent 1D transducers 101a, 101b, 101c (i.e. transducers producing 1D ultrasound rays). The transducers 101a, 101b, 101c are coupled to the body surface of a patient 001 via an acoustic coupling device 104. The position and orientation of a reference transducer 101c is monitored in absolute world (room) coordinates by the position sensor 201b attached to the reference transducer 101c. The positions and orientations of the other transducers 101a, 101b are determined relative to this reference transducer 101c by strain gauge, electromagnetic means etc. From the absolute position and orientation of the reference transducer 101c and the relative positions and orientation of the other transducers 101a, 101b the positions and orientations of the other transducers 101a, 101b in absolute world (room) coordinates can be determined.

The number of ultrasound transducers 101a, 101b, 101c, details of transducer fixation and the details of the position detection unit 202 are to be understood in no way limiting or restrictive.

Position Detection System 201a, 201b, 201c, 202

Each ultrasound transducer 101a, 101b, 101c is attached to a position sensor 201a, 201b, 201c capable to detect the transducers location and orientation relative to a fixed frame of reference or relative to another positioning detector. These sensors are coupled to a position detection unit 202 which calculates the 3D positions and orientations of the individual ultrasound transducers 101a, 101b, 101c in real-time or near real-time relative to a fixed frame of reference or another moving frame of reference, registered to some fixed frame.

The positioning system defines a stereotactic space which is the reference coordinate system for all parameters determined in the parameter extraction unit 400. All of the calculated coordinates for the physiologic output values of the parameter extraction unit 400 are referenced to this space.

The basic requirement for the position detection system is that it determines the individual positions and orientations of all ultrasound transducers 101a, 101b, 101c within the defined stereotactic space in real-time and in three-dimensions of space. This can be achieved in several different ways. As an illustration some embodiments are described in the following. However, these examples are by no means limiting or restrictive.

In one preferred embodiment the position and orientation detection is realized by an optical tracking system using visible or infra-red light. The system can be realized by observing the ultrasound transducers 101a, 101b, 101c by one or more cameras (standard systems use two cameras combined to a stereo camera system.) and calculating the coordinates and rotations e.g. by triangulation or other means. This position detection can be realized with optically retroreflective or active LED markers or can also be marker-less.

Another embodiment can be realized by an electromagnetic system using e.g. coils or other means mounted to the ultrasound transducers 101a, 101b, 101c as position sensors. These sensors can then be localized in an electromagnetic field of some kind.

In another embodiment the position and orientation detection could be realized using an inertial or acceleration based motion (e.g. based on a gyroscope, coriolis force etc.) sensor built into or attached to the ultrasound transducers 101a, 101b, 101c. Such a system would be able to detect changes in the transducer's positions and view angles. Due to the relative nature (i.e. the measurement of changes rather than absolute angles and positions) an absolute starting value has to be determined by some kind of calibration procedure prior to the measurement.

Another embodiment can use a resistance strain gauge in combination with a belt in which the ultrasound transducers 101a, 101b, 101c are fixed in their position relative to each other.

Another embodiment can be realized by a mechanical device to measure angles and positions in some way. One realization of this kind could be a stereotactic arm or mechanical frame attached to one or more of the ultrasound transducers 101a, 101b, 101c.

Also specialized embodiments of the position detection system can be used for certain operating environments. E.g. for measurements within a magnetic-resonance scanner the magnetic field or the gradient fields can be directly used to determine transducer positions. One possibility would be to use induction coils mounted to each of the transducers 101a, 101b, 101c to take advantage of the position dependency of resonance frequencies to localize the transducers 101a, 101b, 101c. In a magnetic resonance scanning environment also direct field measurements using e.g. the Hall-effect or Kerr-effect can be exploited for transducer localization. In this case Hall or Kerr sensors can be built into the ultrasound transducers 101a, 101b, 101c.

Any of the realizations in the above embodiments can be combined in some way e.g. to enhance localization precision, detection security etc. Also absolute and relative localization measurements might be combined to realize the definition of a stereotactic space. Such a realization could e.g. be the combination of the inertial sensors with some absolute method applied prior to the tracking.

In another embodiment, the absolute position and orientation values for a single reference ultrasound transducer 101a 101b, 101c are determined. For the other transducers 101a, 101b, 101c relative positions and angles are determined with respect to the reference transducer. One variant of the embodiment can also be the relative measurement of transducers 101a, 101b, 101c in a belt when one transducer 101a, 101b, 101c is in a defined position to the patient table to get correlation with a coordinate system of another modality or accelerator (calibration)

The position sensor configuration depicted here is merely illustrative and can vary depending on the exact nature of the position detection system.

Transform Unit 300

The ultrasound data from each ultrasound transducer 101a, 101b, 101c paired with the localization data from each position sensor 201a, 201b, 201c are transferred to a transform unit 300 which calculates a coordinate transform for the ultrasound data from each transducer 101a, 101b, 101c to register the data from all transducers to a common fixed or non-fixed frame of reference. In an alternative embodiment, the transform unit can equivalently transform coordinates measured in the fixed frame to the moving coordinate system of each individual transducer 101a, 101b, 101c.

The data transformation system uses the position and orientation data for the ultrasound transducers 101a, 101b, 101c from the position detection system to calculate transformation matrices for each of the ultrasound datasets to a common frame of reference. With these transformation matrices any parameter x determined with respect to the coordinate system of the ultrasound transducers 101a, 101b, 101c can be transformed to the common system x' by a linear (affine or similar) Transform M: $x'=M*x$. where M contains translation and rotation information for the coordinates.

The common frame of reference can either be fixed or moving. E.g. in case of an application together with a medical imaging system this common reference frame can be the native coordinate system for the imaging system. In this case the transformation matrix or function can be defined by coregistering one reference dataset of the ultrasound data to an image volume from the medical imaging system.

In case of the application with a radiotherapeutic device the common coordinate system is preferably chosen as the iso-center of the radiation beam and/or as defined by the radiation plan.

The frame can also be another moving frame e.g. defined by patient markers of any kind to enable measurements relative to a patient coordinate system.

Parameter Extraction Unit 400

The output of the transform unit 300 are ultrasound data in a common frame of reference which are subsequently used by the parameter extraction unit 400 to calculate three-dimensional, quantitative physiologic information of the observed object of interest 002. In a preferred embodiment, the extracted parameters comprise displacement (e.g. deformation, translation and rotation) information of organs or other physiologic or patho-logic structures observed by one or more of the attached ultrasound transducers 101a, 101b, 101c.

The parameter extraction system receives the transformed 1D, 2D or 3D ultrasound data from the transducers 101a, 101b, 101c as output of subsystem 300 to calculate quantitative measures of the physiologic state of the observed object of interest 002 and provide a control signal as an input for the medical device 500. In principle any physiologic data obtainable from ultrasound data can be extracted.

Exemplary embodiments of a dedicated parameter extraction unit 400 could e.g. produce trigger or control signals from ultrasound Doppler signals, e.g. when certain flow changes (e.g. flow reversal, flow deceleration, acceleration or similar) occur in certain regions of space.

Other embodiments can also produce signals from ultrasound data in combination with ultrasound contrast agents, e.g. when certain signal enhancements (due to destruction of contrast micro-bubbles, non-linear responses or similar) occur.

Also a dedicated parameter extraction unit 400 could be implemented to generate control signals from ultrasound data of the heart (echocardiography) e.g. resembling or correlating to the electrical state of the heart as usually generated by electrode based electro-cardiography (ECG) systems.

In a preferred embodiment the parameter extraction unit 400 is used to generate quantitative information on motion (displacements, deformation, rotation) of the structures of interest 002 from linearly independent 1D, 2D or 3D ultrasound imaging data.

In a simple design embodiment, the streaming ultrasound data could be e.g. registered or correlated frame by frame so that information on the deformation, translation and rotation of the object of interest 002 in the ultrasound data can be extracted e.g. from a (affine or the like) registration transformation matrix. Also speckle tracking can be used to detect object motion.

A preferred design embodiment of the parameter extraction unit 400 uses a 3D reference model of certain structures of interest observable in the ultrasound data to localize and track objects 002. These structures can either be anatomical or pathological features or can also originate from the ultrasound method itself an e.g. speckle structures. The reference model can consist of data volumes or point sets reflecting the location of prominent areas, contour lines of structure borders or internal parts and can be a an open or closed 2D surface of the complete or part of the object of interest 002 to be tracked.

The coordinate system of the 3D reference model is defined such that location and orientation of the model structures are represented in a previously defined reference coordinate system which coincides with the reference frame of the position detection system 201a, 201b, 201c, 202. In this way all ultrasound data can be transformed to this coordinate system by the transform unit 300 and thereby are in registration with the 3D reference model. The reference frame can e.g. be the native frame of a medical imaging device, the isocenter frame of a radiation therapy vault, a frame defined by a surgical instrument or the patient 001, etc.

The 3D reference model can be generated from external medical imaging data (e.g. CT, MR, PET) e.g. by structure segmentation or manual delineation of organ boundaries or other structural features. Alternatively, it can be defined by some user input e.g. by drawing contours or by fitting a previously defined generic mathematical organ model or template. Also a 3D reference model can be generated from ultrasound data directly e.g. from typical speckle patterns.

In a preferred application for motion correction in radiation therapy, the 3D reference model can originate from a radiation therapy plan. A therapy plan contains structures at risk and/or isodose lines defined from CT imaging prior to radiation therapy. In the planning stage the physician chooses such structures from anatomical and pathological features in the planning CT and stores them as line structures in a digital form. Part of these contour lines can then define the 3D reference model as a prerequisite for the structure displacement determination. The radiation therapy plan by definition also determines the isocenter system of the radiation therapy device which consequently is used as common reference frame for the reference model and the ultrasound data. When the positioning system of the position detection system 201a, 201b, 201c, 202 is calibrated to match the isocenter system the structures in the therapy plan already match the ultrasound data closely—besides residual errors due to repositioning errors of the patient 001 prior to therapy. These residual errors then reflect the movement of the patient 001 or internal structures in different therapy fractions. Once quantified this initial displacement can be eliminated by moving the patient 001 in the correct isocenter position so that the 3D reference model of the structures at risk matches the ultrasound. If the patient 001 or internal patient structures 002 move during therapy, this is reflected in a mismatch between the ultrasound data and the 3D reference model. These mismatches can be quantified by the parameter extraction unit 400 and used as control input for the radiation therapy device.

Figure 5:
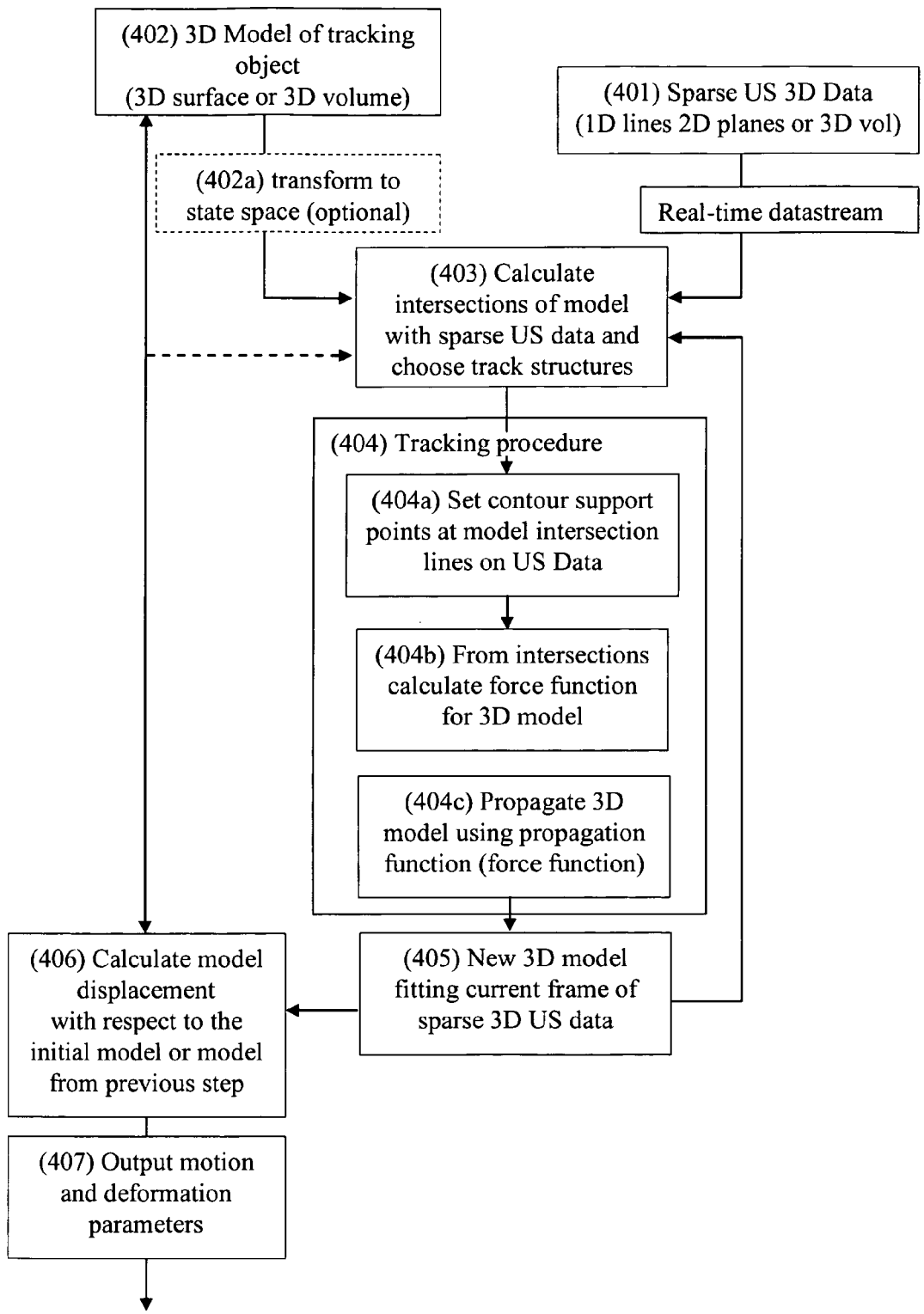
FIG. 5 shows an embodiment of the parameter extraction unit to generate motion information using an active contour approach.

The principle workflow of a preferred embodiment for motion detection and tracking is depicted in FIG. 5. The embodiment uses active contours generated from the input 3D reference model to track motion.

An initial 3D (reference) model 402 (as stated above) is supplied to the unit together with a continuous stream of sparse 3D ultrasound data 401 consisting of 1D rays, 2D images or 3D volume data.

For an initial time frame the intersections between the ultrasound data and the model are calculated 403. Depending on the dimensionality of the ultrasound data these can either be 2D contour lines (for 2D US data) or single points (for 1D US data). Subsequently, along these intersection lines support points for an active contour are chosen (either automatically or manually by user input) 404a. This contour can then be tracked using some algorithm e.g. based on active contours 404. In an exemplary realization a global force function is calculated from an internal energy in the individual ultrasound datasets 404b. Based on this force function the 3D model can then be transformed frame by frame to maximally fit the sparse ultrasound data 404c. From this procedure a new model can be propagated 405. By comparison of the propagated model 405 either with the initial model 401 or with the model from the previous step (model before 404) motion and deformation parameters can be calculated 406 and transferred to the output of the system as control information for other medical procedures 407.

As a variant to increase robustness of the method the contour can be transformed to a state space prior to tracking 402a. Such a state space can reflect typical transformations of the object of interest 002 e.g. as affine or eigenmode transforms or other typical transforms determined from learning sets acquired previously. This state space transformation has the advantage that the dimensionality of the tracking space can be greatly reduced from O (number of contour points) to O (degrees of freedom of state space) resulting in a better tracking for noisy data.

The details of the 3D model tracking procedure 404 in FIG. 5 are to be understood as an illustration of one possible method only and are in no way limiting: The exact propagation algorithm can vary in certain embodiments.

Figure 6:
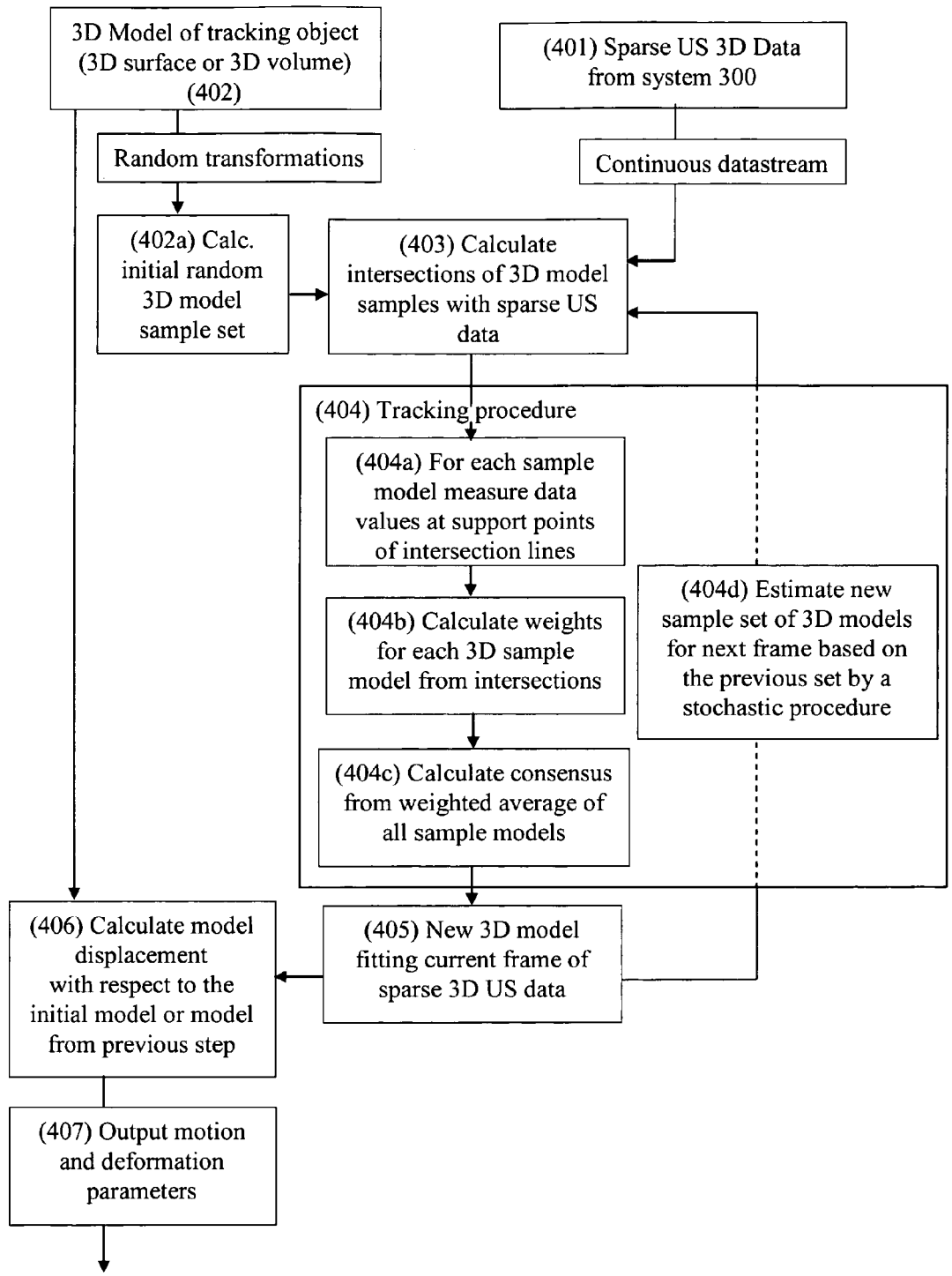
FIG. 6 shows a preferred embodiment of the parameter extraction unit to generate motion information using a robust stochastic tracking approach.

A further variant of this method for robust tracking on noisy and cluttered ultrasound data uses a combination of active contours (as determined from said 3D model) and a stochastic tracking approach. The outline of an exemplary procedure of this kind is depicted in FIG. 6. This procedure is to be understood as an exemplary embodiment.

As above an initial data fitting 3D model 402 is supplied to the unit together with a continuous stream of sparse (or complete) 3D ultrasound data 401 consisting of 1D rays, 2D images or 3D volume data.

The tracking procedure is initialized by calculating a collection of different transformed models from the initial 3D model by random choice (called "sample set" in the following). The transformations of the model can either be done in real space (i.e. with respect to the reference coordinate system for each point individually) or in a state space—allowing only certain (e.g. affine or tissue model based) model transforms as stated above (FIG. 5, 402a). Due to robustness the latter is preferred.

Subsequently, the intersection of each of the transformed models (sample) with the current frame of each ultrasound transducer 101a, 101b, 101c is calculated 403 and support points for an active contour are assigned to the intersection lines for each sample. The 3D model is then propagated using a probabilistic approach in a tracking loop 404. At the support points chosen from the intersection lines local measurements are taken from the ultrasound data to determine a value that reflects the goodness fit with the particular model point 404a. The measurement value can e.g. be a grey value (or possibly RF value), a gradient value or similar of the ultrasound data at the respective point.

From the local measurements at the support points a global value for each individual model transformation is then calculated, representing a weight for the particular transform 404b. This weight is a measure for the likelihood of the respective 3D sample to be the "correct" (i.e. optimum feature fitting) model for the current ultrasound frame as compared to the other samples in the set. Such a sample weight e.g. can be calculated by summing up the grey values in the ultrasound data along the respective sample intersection lines. Other more complicated weight functions are equally possible.

A weighted average of all samples in the set i.e. from all jittered 3D models is then calculated according to the weights obtained from the ultrasound values 404c. This average then represents a consensus 3D model chosen as the best fit for the current ultrasound data frame 405.

The sample set, the weights and the average model for the current data (or a subset of these) are then used to propagate the model to the next frame 404d. In a preferred embodiment this propagation can be done by an autoregressive diffusion process. In an exemplary implementation of this kind a prior sample forms the base estimation for the new frame with a probability according to its previous weight. Samples with highest weights in the last frame are then most likely to be chosen for the sample set in the next frame. A process of this kind is iterated over all samples (or a subset of these) in the prior set to generate a new complete (or reduced) sample set for the next image frame. The propagation process 404 is repeated for consecutive ultrasound frames to track the model in real-time or near real-time.

In similar embodiment to speed up calculation no complete intersection calculation of the 3D model with the ultrasound data is calculated but the distance of each object point to the ultrasound image planes is calculated and only a number of N closest points is used.

A modification of the stochastic procedure depicted in FIG. 6 is to calculate the intersection with one representative 3D model only (as opposed to the use the intersections of a 3D model set). Subsequently, from the intersection of this model with the ultrasound data a contour is constructed for the data from each ultrasound transducer 101a, 101b, 101c, separately. From this, a contour sample set can be randomly chosen, so that for each ultrasound dataset an individual sample set is constructed which can then be propagated in a similar procedure as stated above.

Figure 7:
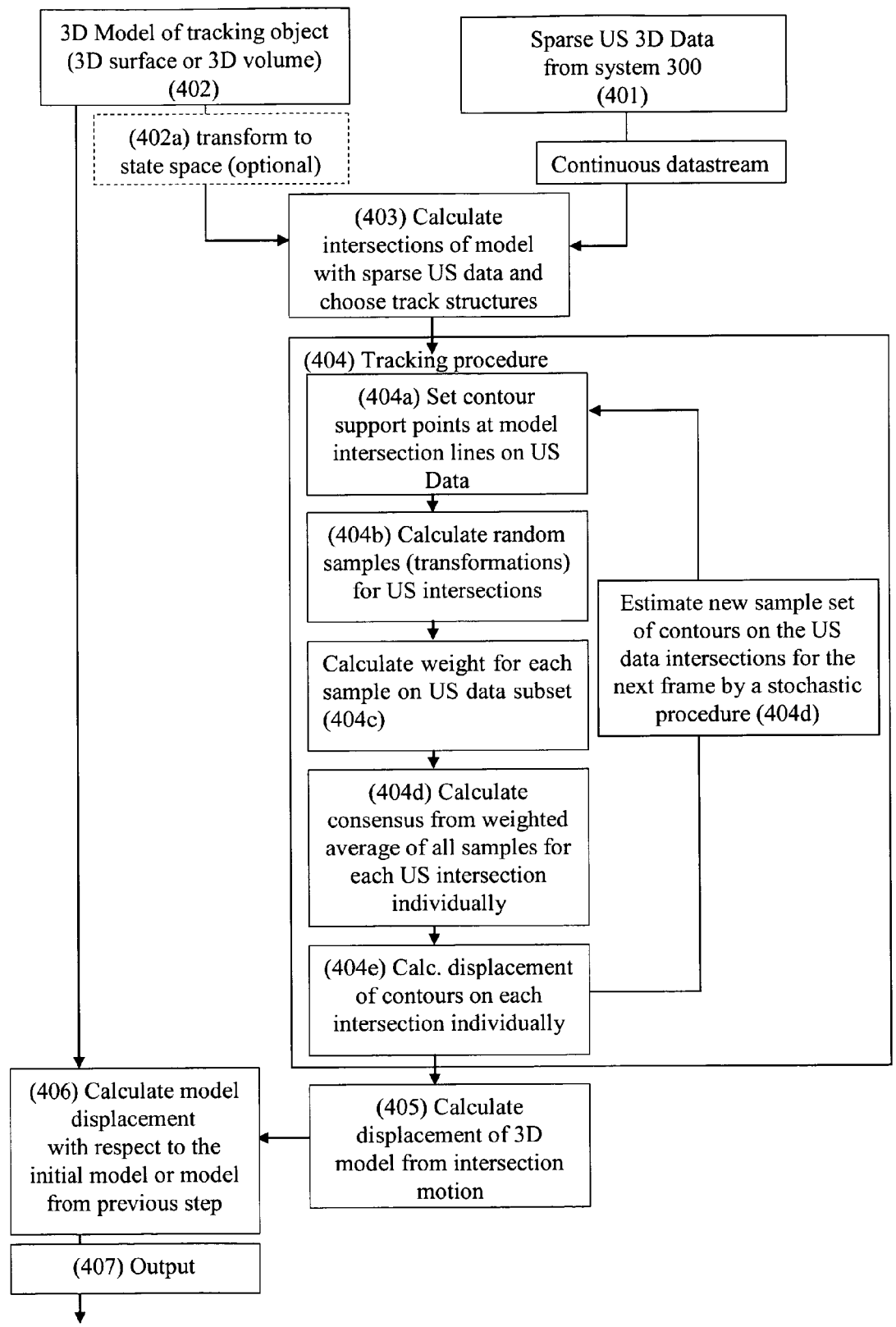
FIG. 7 shows an alternative embodiment of the parameter extraction unit with motion tracking on intersection lines.

As a result, displacement parameters are determined for the contours on each intersection individually. In a later stage, the position and orientation information from the individual views can be combined to determine the motion and deformation of the representative 3D model. To illustrate the principle of this procedure an exemplary embodiment of this kind is depicted in FIG. 7.

In other embodiments, the tracking procedure does not have to be exclusively done on the software side. With specialized ultrasound hardware it is also possible to track structures of interest with the ultrasound beams (or planes) themselves by adjusting the beam (or US plane) position and direction. For example for structure tracking a value (e.g. an energy function or force) could be defined which reflects how good the ultrasound beam observes the structure. Such a value can then be used in a feedback loop for the ultrasound beam so that in effect the beam is able to follow the structure (much like a spotlight on a stage). In such a setup motion parameters can be determined by extracting the value of the current beam direction or position.

In the case of a modified embodiment of the stochastic tracking procedure stated above the tracking does not have to be restricted to the tracking of a model on the software side. The construction of a sample set can also be partly shifted to the hardware side. In such an embodiment a sample set might be constructed e.g. by jittering beam or US plane directions and orientations in a random way. For different beam directions a weight could be calculated which corresponds to the likelihood of the beam having a direction fitting the model well. In this way not only the model or the resulting intersection contours are used to construct a sample set but also statistically jittered beam or plane directions of the ultrasound device 101a, 101b, 101c, 102 itself. One possible embodiment to do this is e.g. to use many phased array transducers with a low number of elements in a 2D array to produce a single focused ray from each transducer 101a, 101b, 101c which can be tilted in 2 directions. This makes it possible to produce different beam directions with the ultrasound transducer 101a, 101b, 101c and hence to sample the observed structure in different directions. From a set of different beam directions and the values at a certain intersection point a best fitting beam direction could be calculated in much the same way as stated above. So such transducers 101a, 101b, 101c can be used to aim at the target structure and follow the maximum probability movement.

Medical Device 500

The control signal provided by the parameter extraction unit 400 can be used as trigger, exclusion and inclusion signals or as continuous control signals for other medical devices 500, such as radiation therapy devices, imaging devices or surgical and biopsy instruments.

The application of some preferred embodiments of the arrangement 101a, 101b, 101c, 102a, 102b, 102c, 102, 202, 300, 400 to control a medical device 500 can be illustrated by the following examples:

- The arrangement starts a controlled medical device 500 (e.g. an accelerator) in radiation therapy, when a target structure is in a certain position or is in a certain flow or deformation state.
- The arrangement sends position and orientation of a certain target structure to the medical device 500 (e.g. an adaptive radiation therapy device, e.g. robotic radiation therapy device, particle (proton or hadron) radiation device), to compensate for potential motion in real-time.
- The arrangement detects changes in blood flow in certain regions of a vessel and starts or stops the medical device 500.
- The arrangement measures flow in a certain tissue region so that the medical device 500 can react on the exact value of flow in real-time (e.g. for dose regulation in radiation therapy).
- The arrangement can detect flow, motion and deformation in the heart and e.g. generate an ECG signal from this mechanical and flow information. In this manner it can be used to substitute conventional ECG-trigger systems by real-time detection of cardiac motion.

The solution described above can be also characterized in terms of the following items:

1. An ultrasound device to measure physiologic parameters, (e.g. motion and deformation) in 3D to guide or control other medical devices or procedures in real-time, comprising:
   a) an Ultrasound system providing structural and/or physiologic image data in real time;
   b) one or multiple 3D, 2D or 1D transducers coupled to the ultrasound system providing linearly independent (i.e. acquired from different directions, in multiple non-coplanar planes or non-collinear lines) sparse or complete 3D ultrasound data indicative for the location, deformation or physiologic status of a region of interest;
   c) a device to determine localization and direction information of each ultrasound transducer coupled to the system relative to a fixed frame of reference;
   d) a method to fuse the information of the transducer motion and the information of the organ motion relative to the transducer to extract 3D motion information with respect to a fixed frame of reference;

e) a method to determine 3D physiologic organ (especially motion and deformation) parameters (of a 3D organ model) from linearly independent 1D, 2D or 3D ultrasound imaging data.
2. A particular embodiment of item 1 to track motion and deformation of a particular physiologic structure and to produce control or trigger signals indicative for structure displacements.
3. A particular embodiment of item 2 in which
a 3D model of structures of interest with known coordinates in a fixed frame of reference is used to track motion in the ultrasound data;
the model can comprise organ or lesion structures or boundaries; and
the model is fitted to the ultrasound data and then propagated for each image frame to determine the motion parameters for the model in 3D in the fixed frame of reference.
4. An embodiment of item 2 where the 3D model of the tracking structure is derived from image data acquired by a second imaging modality (e.g. CT/MR/PET) (with known coordinates in the fixed frame).
5. An embodiment of item 2 where the 3D model of the tracking structure is derived from ultrasound speckle patterns.
6. An embodiment of item 2 where the 3D model of the tracking structure is derived from data derived from a radiation plan in radiation therapy.
7. An embodiment of item 2 where the 3D model of the tracking structure is derived from a user input or an abstract model of structures (with known coordinates in the fixed frame).
8. One embodiment of item 1 comprising 2 or more non-coplanar 2D ultrasound transducers to acquire a sparse 3D dataset from 2D slices.
9. One embodiment of item 1 comprising 3 or more non-collinear 1D ultrasound transducers to acquire a sparse 3D dataset from 1D ultrasound rays.
10. One embodiment of item 1 combined with a method to detect position and rotation of each ultrasound transducer with respect to the fixed frame of reference by means of inertia.
11. One embodiment of item 1 combined with a method to detect position and rotation of each ultrasound transducer with respect to the fixed frame of reference by means of optical tracking.
12. One embodiment of item 1 combined with a method to detect position and rotation of each ultrasound transducer with respect to the fixed frame of reference by means of electromagnetic tracking.
13. One embodiment of item 1 combined with a method to detect position and rotation of each ultrasound transducer with respect to the fixed frame of reference by means of combination of inertia, optical tracking and electromagnetic tracking.
14. A method to coregister a 3D organ model to the multiple intersection planes acquired by system from item 2.
15. A method to detect motion or physiologic information on the ultrasound images acquired by system ½ in real-time or near real time and to extract motion parameters and/or quantitative physiologic information.
16. A method to generate trigger and control signals from ultrasound Doppler information with this system.
17. A method to generate trigger and control signals from ultrasound contrast agent information with this system.
18. A method to extract and calculate the motion an deformation parameters (e.g. translation rotation) of the 3D organ model from the ultrasound image data acquired by system ½ with respect to a fixed frame of reference.
19. An embodiment of item 1 which is able to determine motion parameters for the heart and from this mechanical data to extract information on the ecg signal of the heart; and
the extracted signal can be e.g. used as a trigger for medical procedures.
20. An embodiment of item 1 in which the transducers are fixed to a holder (like a clamp or bracket) to view the object of interest from a fixed position and/or angle.
21. An embodiment of item 1 where the ultrasound transducers are fixed to the surface of the object of interest (e.g. patient body) and are allowed to move freely (or partly freely) with respect to a fixed frame of reference.
22. An embodiment of item 1 in which the transducers are fixed to the body and are allowed to move freely with respect to a fixed frame of reference.
23. An embodiment of item 1 in which the transducers are fixed with respect to a fixed frame of reference, e.g. by means of a mount or holder.
24. An embodiment to determine motion and flow information of the heart with this system and to use this as ecg trigger signal.

While the present inventions have been described and illustrated in conjunction with a number of specific embodiments, those skilled in the art will appreciate that variations and modifications may be made without departing from the principles of the inventions as herein illustrated, as described and claimed. The present inventions may be embodied in other specific forms without departing from their spirit or essential characteristics. The described embodiments are considered in all respects to be illustrative and not restrictive. The scope of the inventions is, therefore, indicated by the appended claims, rather than by the foregoing description. All changes which come within the meaning and range of equivalence of the claims are to be embraced within their scope.

REFERENCES 001 body
002 object of interest
101a ultrasound transducer
101b ultrasound transducer
101c ultrasound transducer
102 ultrasound unit
103 ultrasound beam
104 coupling device
105 transducer case
106a transducer array
106b transducer array
201a position sensor
201b position sensor
201c position sensor
202 position detection unit
300 transform unit
400 parameter extraction unit
500 medical device

The invention claimed is:
1. An arrangement to determine physiologic data, position, orientation and geometry of an object of interest comprising:
an ultrasound unit with one or more ultrasound transducers,
a position detection system and
a processing unit,
wherein:

a) the position detection system detects the position and orientation of each of the one or more ultrasound transducers;
b) the processing unit calculates physiologic data, position, orientation and geometry of the object of interest from ultrasound data provided by the ultrasound unit and from position and orientation information provided by the position detection system;
c) the processing unit matches a set of one or more reference models representing certain structures of the object of interest to each frame of ultrasound data provided by the ultrasound unit;
d) the processing unit gains information from the set of one or more reference models to calculate the physiologic data, position, orientation and geometry of the object of interest; and
e) the set of one or more reference models comprises more than one reference model, wherein the processing unit gains the information to calculate the physiologic data, position, orientation and geometry of the object of interest from a weighted average of the more than one reference model.

2. An arrangement according to claim 1, wherein the calculation of the physiologic data, position, orientation and geometry of the object of interest is performed in real-time.

3. An arrangement according claim 1, wherein the one or more ultrasound transducers are attached to the object of interest or to a body encapsulating the object of interest.

4. An arrangement according to claim 3, wherein one or more of the ultrasound transducers can move independently from each other.

5. An arrangement according to claim 3, wherein the freedom of movement of one or more of the ultrasound transducers is restricted with respect to each other.

6. An arrangement according claim 1, wherein the freedom of movement of one or more of the ultrasound transducers is restricted with respect to a frame of reference.

7. An arrangement according to claim 1, wherein the processing unit gains information from a sequence of several sets of one or more reference models, each set matched to a different frame of ultrasound data provided by the ultrasound unit, to determine temporal variations of the physiologic data, position, orientation and geometry of the object of interest, wherein the different frames of ultrasound data are sequentially acquired by the one or more ultrasound transducers.

8. An arrangement according to claim 7, wherein a second set from the sequence of several sets of one or more reference models is built by the processing unit based on a first set from the sequence of several sets of one or more reference models, wherein the first set is matched to a first frame of ultrasound data and the second set is matched to a second frame of ultrasound data, wherein the second frame of ultrasound data is acquired by the one or more ultrasound transducers subsequently to the first frame of ultrasound data.

9. An arrangement according to claim 7, wherein weights for calculating the weighted average of the one or more reference models of a first set from the sequence of several sets of one or more reference models are propagated by the processing unit to calculate the weighted average of the one or more reference models of a second set from the sequence of several sets of one or more reference models, wherein the first set is matched to a first frame of ultrasound data and the second set is matched to a second frame of ultrasound data, wherein the second frame of ultrasound data is acquired by the one or more ultrasound transducers subsequently to the first frame of ultrasound data.

10. An arrangement according to claim 1, wherein the one or more reference models are derived from image data acquired by a second imaging modality, from ultrasound speckle patterns, from a radiation plan, from user input and/or from an abstract model of structures.

11. An arrangement according to claim 1, wherein the one or more ultrasound transducers acquire sparse ultrasound data.

12. An arrangement according to claim 1, comprising one or more ultrasound transducers with three-dimensional data acquisition capabilities, wherein the one or more ultrasound transducers acquire sparse or complete ultrasound data from one or more three-dimensional volumes.

13. An arrangement according to claim 11 comprising two or more non-coplanar ultrasound transducers with two-dimensional data acquisition capabilities, wherein the two or more ultrasound transducers acquire the sparse ultrasound data from two-dimensional slices.

14. An arrangement according to claim 11 comprising three or more non-collinear ultrasound transducers with one-dimensional data acquisition capabilities, wherein the three or more ultrasound transducers acquire the sparse ultrasound data from one-dimensional rays.

15. An arrangement according to claim 1, wherein the position detection system comprises one or more position sensors, wherein each of the one or more position sensors are attached to one of the one or more ultrasound transducers.

16. An arrangement according to claim 15, wherein at least one of the position sensors is electromagnetically non-transparent in order to detect the position and orientation of each of the one or more ultrasound transducers when arranged in an electromagnetic field.

17. An arrangement according to claim 15, wherein at least one of the position sensors is a motion, acceleration and/or ankle sensor.

18. An arrangement according to claim 1, wherein the position detection system comprises one or more optical cameras recording the one or more ultrasound transducers to determine the position and orientation of the one or more ultrasound transducers.

19. A medical device comprising the arrangement according to claim 1.

20. A method to determine physiologic data, position, orientation and geometry of an object of interest comprising:
acquiring physiologic data, position, orientation and geometry of the object of interest from an ultrasound system;
acquiring position and orientation data of the object of interest from a position detection system;
physiologic data, position, orientation and geometry of the object of interest are calculated from ultrasound data and from position and orientation information;
a set of one or more reference models representing certain structures of the object of interest is matched to each frame of ultrasound data;
information gained from the set of one or more reference models is used to calculate the physiologic data, position, orientation and geometry of the object of interest wherein
the set of one or more reference models comprises more than one reference model, wherein the information to calculate the physiologic data, position, orientation and geometry of the object of interest is gained from a weighted average of the more than one reference model.

21. A method according to claim 20, wherein the calculation of the physiologic data, position, orientation and geometry of the object of interest is performed in real-time.

22. A method according to claim 20, wherein information gained from a sequence of several sets of one or more reference models, each set matched to a different frame of ultrasound data, is used to determine temporal variations of the physiologic data, position, orientation and geometry of the object of interest, wherein the different frames of ultrasound data are sequentially acquired.

23. A method according to claim 22, wherein a second set from the sequence of several sets of one or more reference models is built based on a first set from the sequence of several sets of one or more reference models, wherein the first set is matched to a first frame of ultrasound data and the second set is matched to a second frame of ultrasound data, wherein the second frame of ultrasound data is acquired subsequently to the first frame of ultrasound data.

24. A method according to claim 22 wherein weights for calculating the weighted average of the one or more reference models of a first set from the sequence of several sets of one or more reference models are propagated to calculate the weighted average of the one or more reference models of a second set from the sequence of several sets of one or more reference models, wherein the first set is matched to a first frame of ultrasound data and the second set is matched to a second frame of ultrasound data, wherein the second frame of ultrasound data is acquired subsequently to the first frame of ultrasound data.

25. A method according to claim 20, wherein the one or more reference models are derived from image data acquired by a second imaging modality, from ultrasound speckle patterns, from a radiation plan, from user input and/or from an abstract model of structures.

26. A method according to claim 20, wherein the physiologic data, the position and the geometry of the object of interest are calculated from sparse ultrasound data.

27. A method according to claim 20, wherein the position information is gained from electromagnetic signals, from motion, acceleration and/or ankle signals and/or from optical signals.

28. Computer program product having program code means stored on a non-transitory computer readable medium, for performing the method according to claim 20 when the program code means are executed on a computer or on a computer network.

* * * * *